United States Patent [19]

Saringer

[11] Patent Number: 4,716,889
[45] Date of Patent: * Jan. 5, 1988

[54] DEVICE FOR IMPARTING CONTINUOUS PASSIVE MOTION TO HUMAN JOINTS

[75] Inventor: John H. Saringer, Toronto, Canada

[73] Assignee: Toronto Medical Corp., Scarborough, Canada

[*] Notice: The portion of the term of this patent subsequent to Dec. 11, 2001 has been disclaimed.

[21] Appl. No.: 768,518

[22] Filed: Aug. 22, 1985

Related U.S. Application Data

[60] Continuation of Ser. No. 660,704, Oct. 15, 1984, Pat. No. 4,537,083, which is a division of Ser. No. 362,896, Mar. 29, 1982, Pat. No. 4,487,199.

[30] Foreign Application Priority Data

Oct. 23, 1981 [CA] Canada .................................. 388659

[51] Int. Cl.$^4$ ............................................ A61H 1/02
[52] U.S. Cl. ...................................... 128/25 R; 128/26
[58] Field of Search ..................... 128/25 R, 25 B, 26, 128/24 R, 51, 52

[56] References Cited

U.S. PATENT DOCUMENTS 4,487,199 12/1984 Saringer ........................... 128/25 R Primary Examiner—Richard J. Apley
Assistant Examiner—J. Welsh
Attorney, Agent, or Firm—Bachman & LaPointe

[57] ABSTRACT

An apparatus for imparting back and forth motion in a slow rhythmic cycle for mobilizing a human joint. An elongated support is provided with a traveller mounted thereon for reciprocating linear movement relative thereto. The traveller is provided with a connector for operatively engaging a limb of the body adjacent to the joint to be mobilized. A reversible motor is provided for driving the traveller through a reciprocating linear stroke and for reversing the direction of travel of the traveller at any point in its path of travel in response to a sensed predetermined load.

2 Claims, 8 Drawing Figures 4,716,889

DEVICE FOR IMPARTING CONTINUOUS PASSIVE MOTION TO HUMAN JOINTS

CROSS REFERENCE TO RELATED APPLICATIONS

This application is a continuation of U.S. patent application Ser. No. 660,704, filed Oct. 15, 1984, now U.S. Pat. No. 4,537,083, which in turn is a division of U.S. patent application Ser. No. 362,896, filed Mar. 29, 1982, now U.S. Pat. No. 4,487,199.

BACKGROUND OF THE INVENTION

1. Field of the Invention

This invention relates to a portable prosthetic device used to treat a human joint by applying "continuous passive motion".

2. Description of the Prior Art

Dr. Robert B. Salter, Professor and Head of Orthopaedic Surgery at the University of Toronto, and Senior Orthopaedic Surgeon at the Hospital for Sick Children in Toronto, first developed the concept and coined the expression "continuous passive motion". Dr. Salter's work is described in the article "Joints Were Meant to Move—And Move Again" by Ohlendorf in "The Graduate", published by The Department of Information Services, University of Toronto, September/October 1980.

Briefly, according to this concept, a human joint, for example, a knee, elbow, or finger joint, is kept under slow continuous constrained motion as distinct from being held motionless or being moved intermittently. Keeping an injured or post operative joint mobile rather than immobilizing it in a cast is beneficial to the cartilage.

Attempts which have been made to provide machines that exercise joints are designed for intermittent operation and do not supply continuous passive motion.

A primary aim of the present invention is to provide an apparatus which imparts continuous motion to the joint.

SUMMARY OF THE INVENTION

An apparatus, according to the invention, includes an elongated support provided with a traveller mounted thereon for reciprocating linear movement relative to the support. The traveller is provided with a connector for operatively engaging a limb of the body adjacent to a joint to be mobilized. A reversible motor is provided for driving the traveller through a reciprocating linear stroke. The motor also reverses the direction of travel of the traveller at any point in its path of travel in response to a predetermined load.

BRIEF DESCRIPTION OF THE DRAWINGS

Having thus generally described the invention, it will be referred to more specifically by reference to the accompanying drawings, which illustrate preferred embodiments, and in which.

DESCRIPTION OF THE PREFERRED EMBODIMENTS

Figure 1:
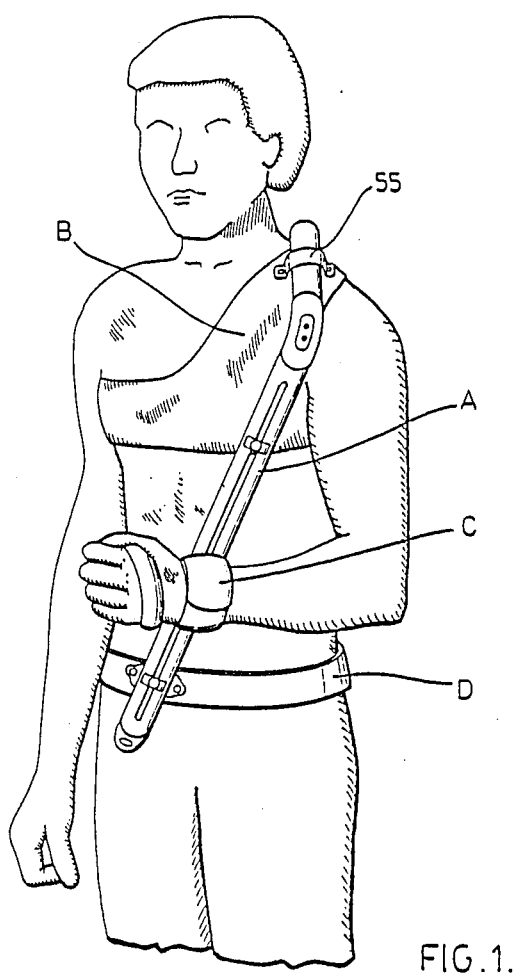
FIG. 1 is a perspective view showing a unit for treating an elbow joint.

Referring more particularly to FIG. 1, the device is made up of a support structure which, in this case, is an elongated housing A connected to the shoulder by a harness B and to the waist by a belt D. Actuator or traveller means, movable relative to the housing, is connected to the wrist by a cuff C. The traveller means is supported by the housing for linear reciprocating movement relative to it. Motor means drives the traveller means back and forth through a predetermined stroke in a slow rhythmic cycle. This imparts a corresponding reciprocating motion to the arm thus imparting continuous passive motion to the elbow joint.

The speed of movement of the actuator means would, in the embodiment shown, range from one-half foot to four feet per minute, or from one-third to two cycles per minute.

Figure 2:
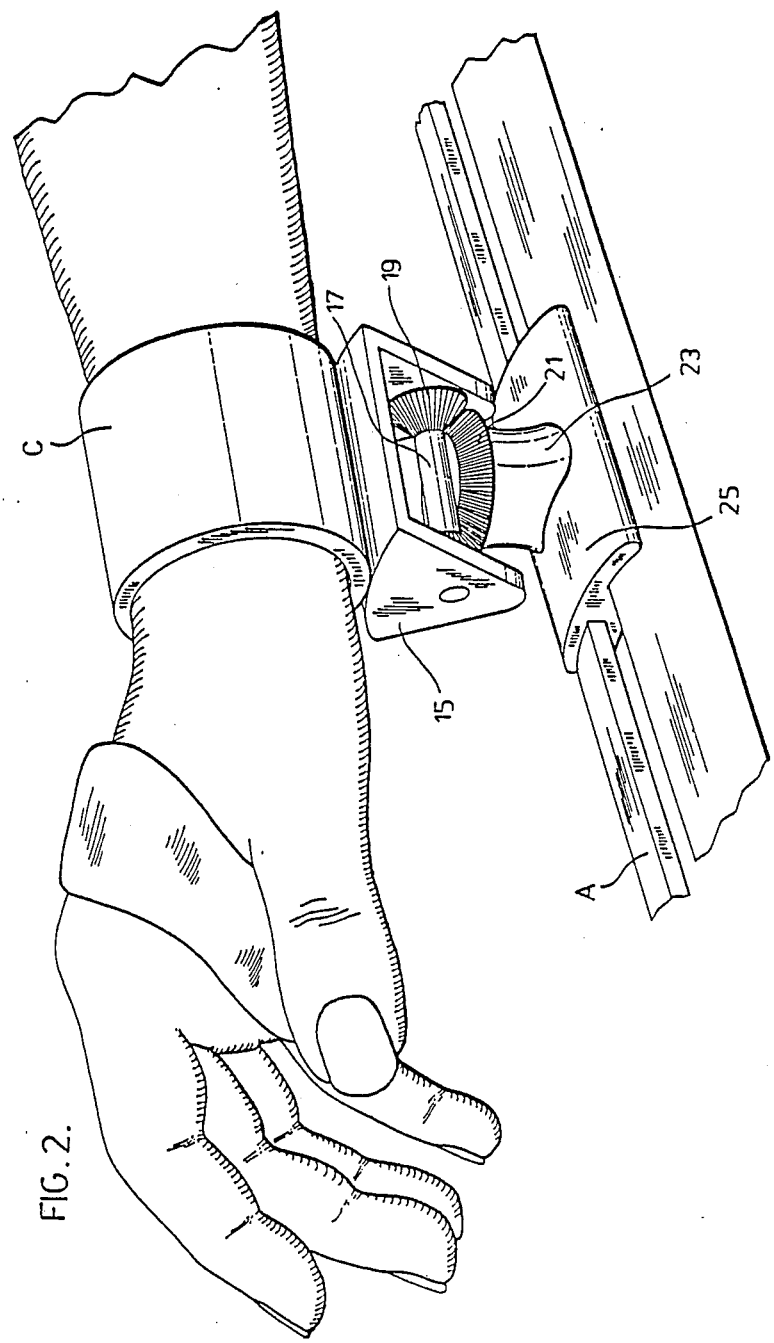
FIG. 2 is a greatly enlarged fragmentary perspective view showing the wrist connection in the unit of FIG. 1.

In order to supply supination and pronation to the wrist, the cuff C is connected (see FIG. 2) to a special mechanism. Mounted for rotation on a U-shape bracket 15 is a shaft 17, carrying a bevel gear 19, which meshes with a crown gear 21, carried on a hub 23, mounted on a plate 25 forming a part of the traveller means.

The plate 25 moves back and forth, along the housing A, and the flexing of the elbow causes rotation of the arm at the wrist, by virtue of its connection to the bevel gear 19 as it is caused to ride around the crown gear 21. At the same time, the wrist is held to the plate 25 so that it makes longitudinal movements with the latter along the housing A.

Figure 3:
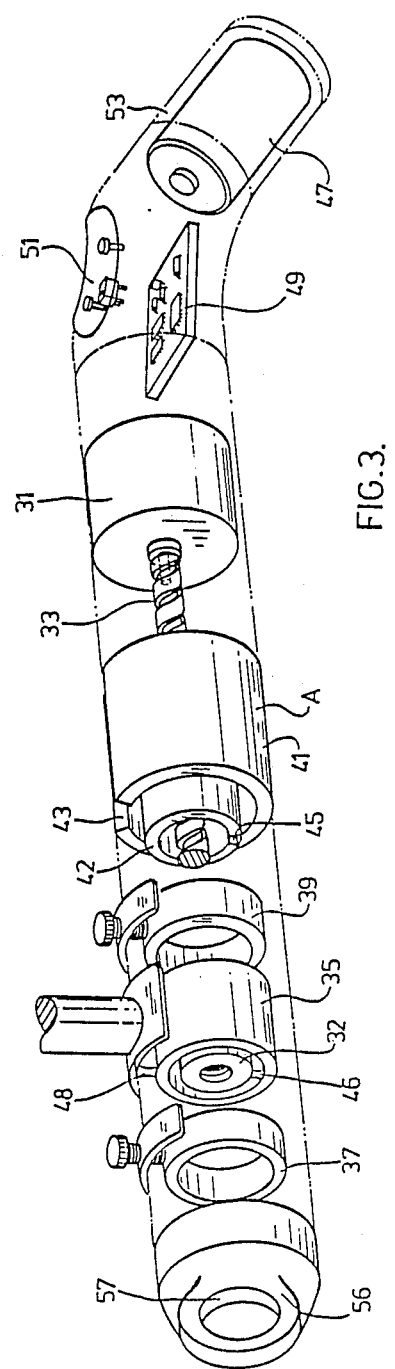
FIG. 3 is a schematic perspective diagram, of an exploded nature, showing the arrangement of the parts in a unit.

FIG. 3 shows in detail the support housing, actuating means, motor means and associated parts. A motor 31 drives an elongated screw 33 whose opposite end is rotatably held in a recirculating ball-type nut 32. A cylindrical slide 35 is connected to the nut 32 and moves linearly under the drive of the screw 33 between the limiting stops 37 and 39, which are locked to the housing A by thumb screws.

The mechanism is encased in an outer tube 41 and an inner concentric tube 42. The tube 41 is provided with a longitudinal slot 43 and the concentric tube 42 with an elongated slot 45. The slot 43 accommodates the flange connection 48 between the slide 35 and the plate 25. The slot 45 accommodates the flange connection 46 between the ball nut 33 and the slide 35.

The motor 31 is powered by batteries 47 which operate through circuits on a circuit board 49 and is governed by controls 51. The tube 41 is provided with a gooseneck part 53 about which there extends a bracket 55 connecting it to the harness B. The other end of the tube 41 has a terminal 56 provided with an eye 57 so that it can be hung from a suitable hook when required.

The motor 31 is a reversible motor. It will reverse as soon as an excessive load is applied. This may be, for example, where the actuator or traveller reaches the end of its stroke and is halted by the stop 37 or 39 as the case may be. Or, it may be where there is some unplanned obstruction, for example, sheets jamming in the mechanism or where the patient offers undue resistance. A safety function is thus performed as well as a prime actuating function.

Examples of suitable motors are geared D.C. Brush type motors made by Faulhaber, Escap, and Maxon Precision, all of Switzerland.

Figures 4, 5:
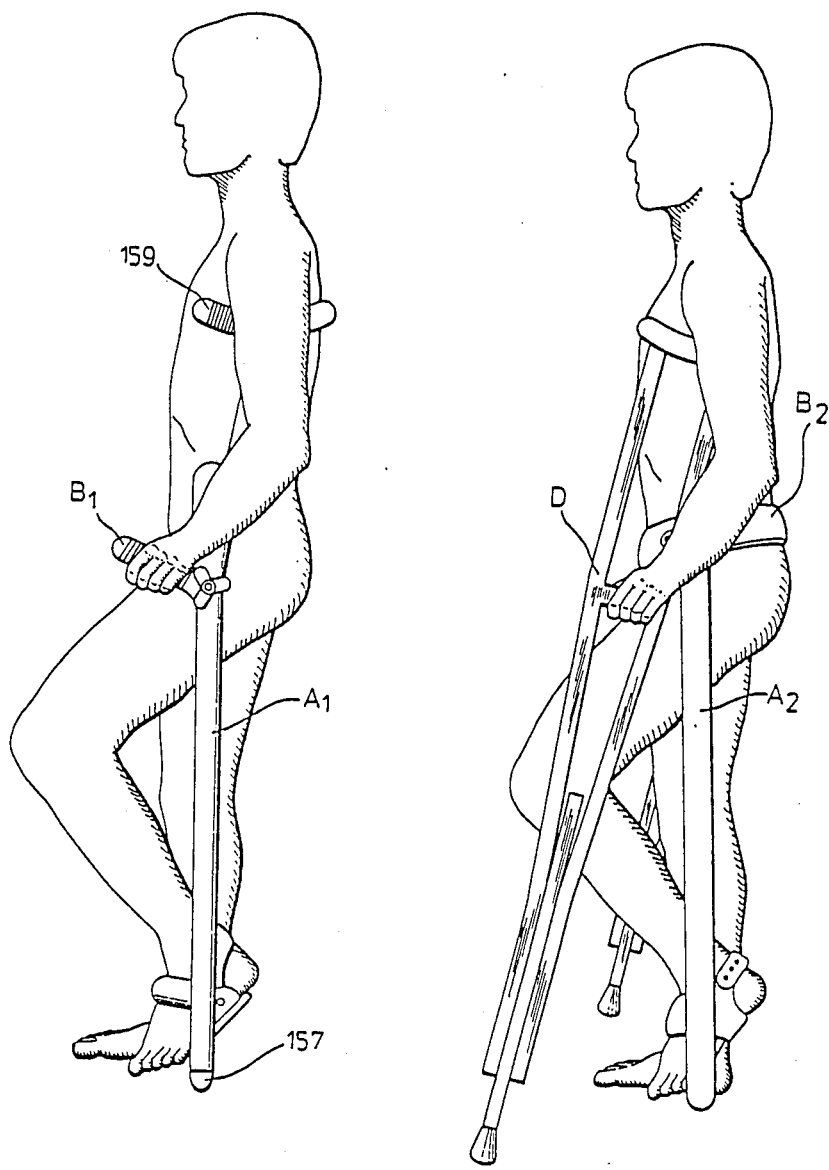
FIG. 4 is a side elevation showing a unit for treating the knee joint in which the unit forms part of a crutch.
FIG. 5 is a side elevation of a variation of the unit of FIG. 4.

FIG. 4 describes an apparatus for flexing the knee joint. Similar numbers have been applied to similar parts, as on FIGS. 1 and 3, with the exception that they have been raised by 100 and the letters have been given a subscript 1.

In this case, the support housing $A_1$ forms part of a crutch for supporting the patient and embodies operating mechanism similar to that shown in FIG. 3, except that the housing $A_1$ is straight instead of having a gooseneck end. It has a rubber foot 157 taking the place of the terminal 56. A handle $B_1$ takes the place of the harness B and is provided with an armpit bar 159. The part $B_1$ slides on the top end of the support housing $A_1$. Taking the place of the plate 25 is a simple foot plate with straps, as compared with the supination and pronation mechanism for rotating the wrist.

FIG. 5 shows an alternative arrangement in which a waistband $B_2$ is employed to connect the top of a support housing $A_2$ to the body. A separate crutch D supports the patient.

Figure 6:
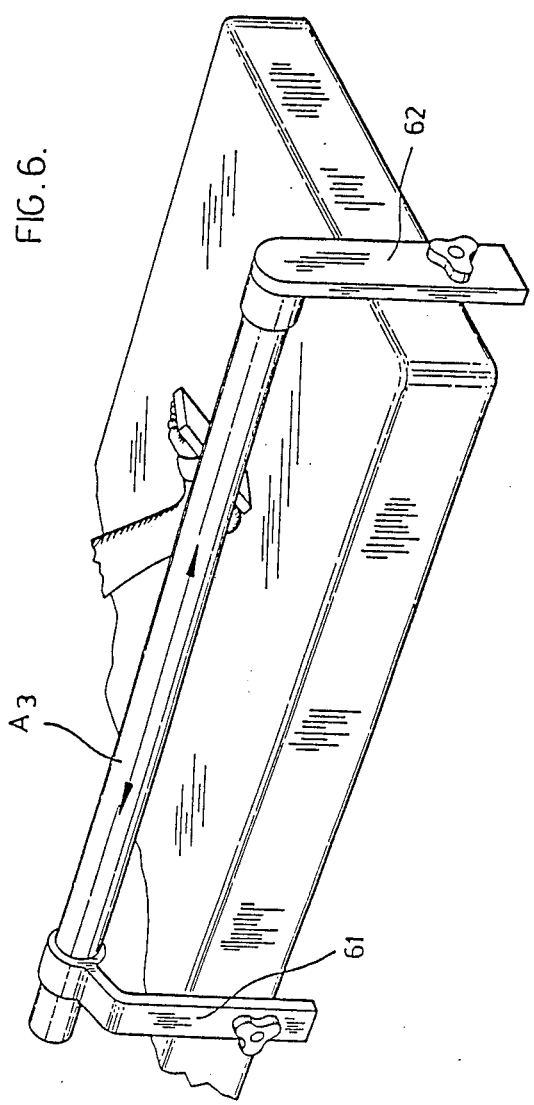
FIG. 6 is a fragmentary perspective showing an operating unit for treating the knee joint and which is connected to a bed on which the patient is reclining.

FIG. 6 illustrates a further form of leg exercising device. In this case, the support housing of FIGS. 4 and 5 is connected to a bed. It is retained by spaced-apart brackets 61 and 62. The leg of a patient lying on the bed is connected to the foot plate as in FIGS. 4 and 5.

Figure 7:
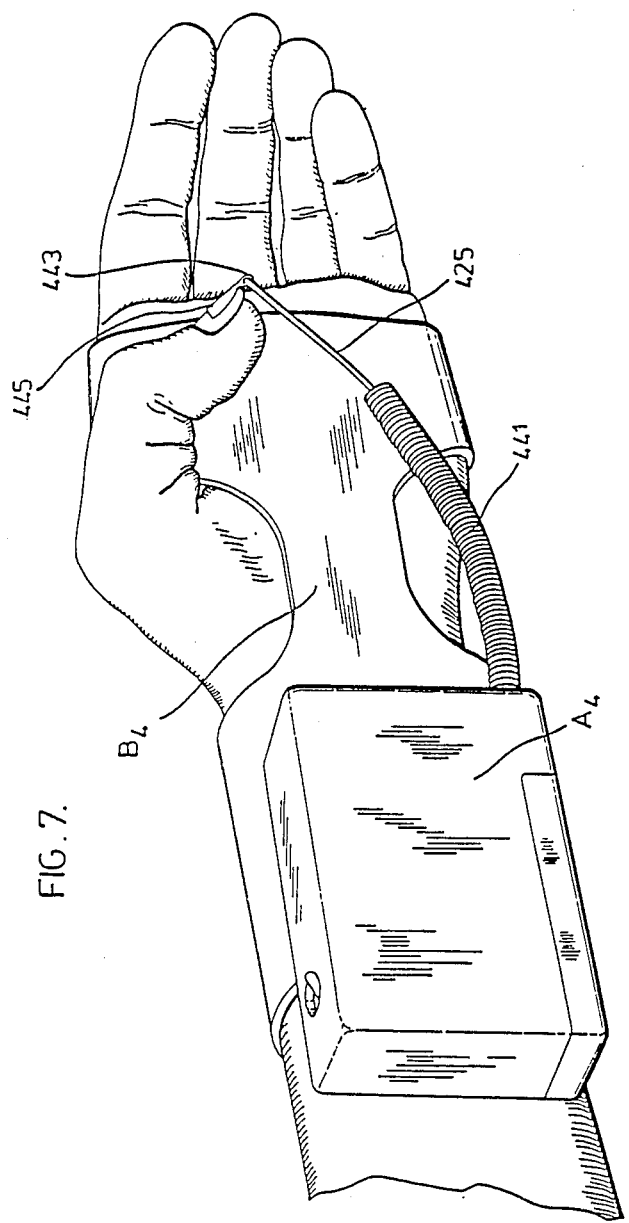
FIG. 7 is a fragmentary perspective view showing a unit for treating a finger or thumb joint.

FIG. 7 illustrates a device for flexing finger or thumb joints. Here again a support housing $A_4$ is connected to a cuff $B_4$ mounted on the wrist and hand in place of the harness of FIG. 1. An actuator wire 425 moves back and forth from the housing $A_4$, through a flexible guide tube 441, to a connection with the thumb.

The connection from the actuator wire 425 to the thumb is through a hinge 443 to a small plate 445, adhesively connected to the thumbnail. Alternatively, the actuator member 445 can be connected to any of the fingers or several fingers at a time.

Figure 8:
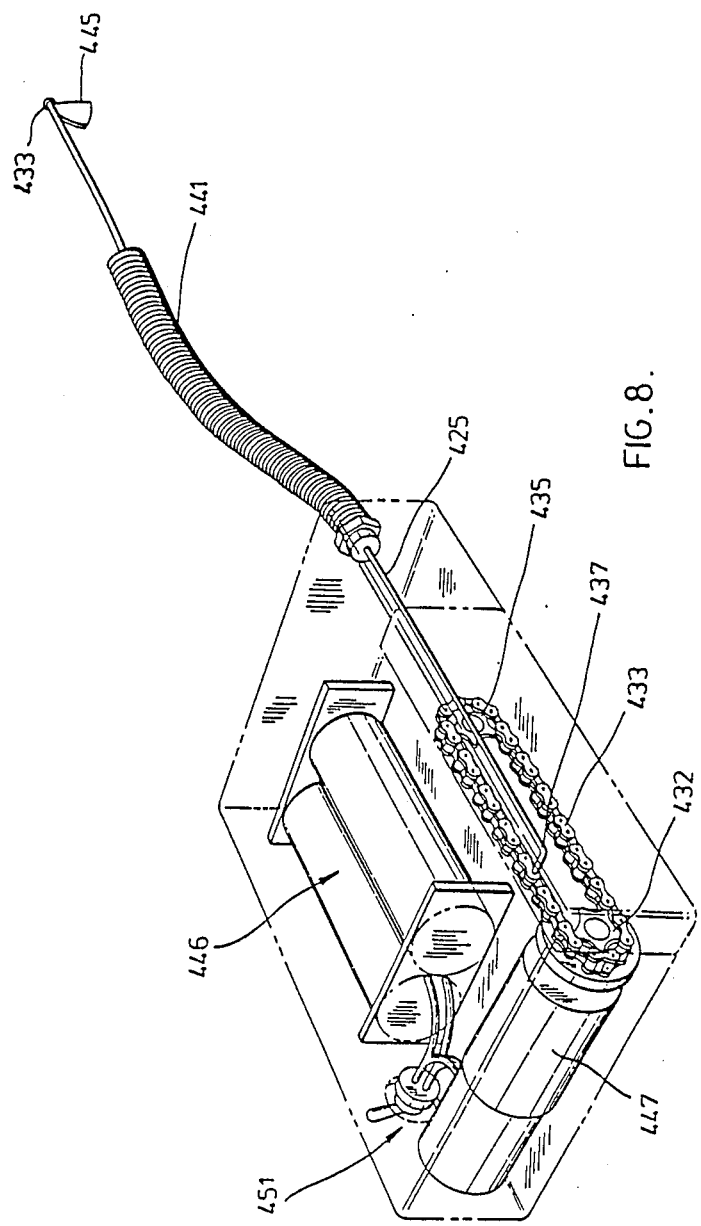
FIG. 8 is a perspective view of the unit shown in FIG. 7, illustrating the drive mechanism.

A mechanism for moving the actuator wire 425 is shown in FIG. 8. The support structure is fashioned from a block of plastic in which recesses have been made to accommodate the various parts. A geared motor 447 drives a sprocket 432 about which there is trained a chain 433 which is also trained about a spaced-apart sprocket 435. The actuator wire 425 is connected at 427 to one of the links of the chain 433. Batteries 446 are accommodated within the block as is an operating switch 451. The motor moves the chain continuously so that the actuator wire 425 moves in one direction along the top run of the chain and then down along the bottom run in the other direction so as to impart substantially continuous reciprocating movement to the wire 425 and consequently to the hand joint.

From this detailed description it will be evident that various modifications can be made within the spirit of the invention to treat various joints of the body under appropriate conditions.

I claim:

1. A continuous passive motion apparatus for mobilizing a human joint, comprising,
    an elongated support,
    traveller means on the support for reciprocating linear movement relative thereto, and means connected to the traveller means for operatively engaging a limb of the body adjacent to a joint to be mobilized,
    motor means for driving the traveller means back and forth through a reciprocating linear stroke in a slow rhythmic cycle; and,
    for reversing the direction of travel of the traveller means at any point in its path of travel in response to a predetermined load.

2. An actuator for imparting back and forth motion in a slow rhythmic cycle, comprising,
    an elongated support,
    traveller means on the support for reciprocating linear movement relative thereto provided with a connector for connecting to means for operatively engaging a limb of a body adjacent to a joint to be mobilized,
    motor means for driving the traveller means,
    transmission means acting between the motor means and the traveller means for driving the traveller means back and forth through a reciprocating linear stroke in a slow rhythmic cycle; and,
    for reversing the direction of travel of the traveller means at any point in its path of travel in response to a predetermined load.

* * * * *